United States Patent

De Jong et al.

[11] Patent Number: 5,723,703
[45] Date of Patent: Mar. 3, 1998

[54] PURIFICATION OF ALLYL CHLORIDE

[75] Inventors: Abe Wiebe De Jong; Timothy Michael Nisbet, both of Amsterdam, Netherlands

[73] Assignee: Shell Oil Company, Houston, Tex.

[21] Appl. No.: 504,277

[22] Filed: Jul. 19, 1995

[30] Foreign Application Priority Data

Jul. 22, 1994 [EP] European Pat. Off. ............ 94202144

[51] Int. Cl.$^6$ ................................................. C07C 21/067
[52] U.S. Cl. ........................................ 570/231; 570/189
[58] Field of Search ................................. 570/231, 189

[56] References Cited

U.S. PATENT DOCUMENTS 3,914,167  10/1975  Ivy et al. ........................ 204/157.98
4,900,849   2/1990  Saletan .................................. 549/521

FOREIGN PATENT DOCUMENTS

537846 A1  10/1992  European Pat. Off.
94/13611    6/1994  WIPO.

Primary Examiner—Alan L. Rotman
Assistant Examiner—Lyman H. Smith

[57] ABSTRACT

A process for the removal of (cyclo)aliphatic hexene and hexadiene isomers from allyl chloride, characterized by a chlorination step which is performed in the liquid phase.

6 Claims, No Drawings

PURIFICATION OF ALLYL CHLORIDE

FIELD OF THE INVENTION

The present invention relates to the purification of allyl chloride by removal of certain undesired by-products.

BACKGROUND OF THE INVENTION

Allyl chloride is commercially prepared by the high-temperature chlorination of propene. Its main use is in the production of dichlorohydrin, which term refers to the isomers 1,2-dichloro-3-hydroxypropane and 1,3-dichloro-2-hydroxypropane, generally by reacting an allyl chloride feed with water and chlorine in a dilute aqueous phase. The main use of dichlorohydrin is for preparing epichlorohydrin (1,2-epoxy-3-chloropropane), generally by dehydrochlorination in the presence of a base. These reactions may be carried out batchwise, semi-continuously or continuously. Other uses of allyl chloride are for the production of esters, allyl ethers and allyl amines (Ullman's Encyclopedia of Industrial Chemistry, 5th Edition, vol. A 1985 page 431).

Aqueous effluent emerging from the epichlorohydrin production processes can contain appreciable amounts of other chlorinated organic compounds (Extractable Organic Chlorine, EOCl, up to about 100 mg Cl/l). These chlorinated organic by-products are mainly chloroaliphatic ethers and chloroaliphatic alkanes. Since the removal of the chlorinated organic by-products from the epichlorohydrin plant effluent by conventional methods, such as fractional distillation, is very expensive, there exists a need for an alternative method for reducing their level.

The present applicant's EP-A-0 359 331 is directed to a method of reducing the level of chlorinated organic by-products in the above-described reaction effluent by extracting the aqueous product of the reaction of allyl chloride with water and chlorine, with a water-immiscible solvent having an atmospheric boiling point of from 40° C. to 105° C. The present applicant's EP-A-0 537 846 discloses a similar method wherein the extracting water-immiscible solvent is 1,2,3-trichloropropane.

In the present applicant's WO-94/1316 a different approach to reducing the level of chlorinated organic by-products in the above-described reaction effluent is presented. Therein it is disclosed, that the above undesirable chlorinated organic by-products are mainly chloroaliphatic ethers having 9 and 12 carbon atoms ($C_9$ and $C_{12}$), the level of the $C_{15}$ chloroaliphatic ethers being much lower, and that their source in the allyl chloride feed is mainly hexadienes (i.e. $C_6H_{10}$ isomers, in particular 1,5-hexadiene, 1,4-hexadiene and 2-methyl-1,4-pentadiene), which are by-products of the high temperature chlorination of propene to allyl chloride. When present in the allyl chloride feed to the above-described reaction with water and chlorine to form dichlorohydrin, these hexadienes also react with chlorine, water and dichlorohydrin to form the chloroaliphatic ethers found in the reaction effluent.

The commercial allyl chloride used for the production of dichlorohydrin is at least 97.5 wt % pure and contains hexadiene as an impurity (Ullman's Encyclopedia of Industrial Chemistry, ibid.). In order to reach this degree of purity, the crude allyl chloride as produced by the chlorination of propene and which contains about 75–80% of allyl chloride plus lighter and heavier impurities, is conventionally purified. The purification is generally performed by distillation, in at least two steps, wherein light and heavy ends respectively are removed. Normally, 0.3–1.0 wt % of hexadiene is still present in the purified allyl chloride used for the production of dichlorohydrin. In WO-94/1316 it is disclosed that when an allyl chloride feed containing less than 0.30 wt % of hexadiene is used with water and chlorine for the production of dichlorohydrin, the product contains much less of the undesirable chlorinated organic by-products, which substantially reduces the costs of purifying the aqueous effluent leaving the plant.

WO-94/1316 proceeds to disclose several methods for removing the hexadienes from the allyl chloride feed for the dichlorohydrin production, with a view to reducing the production of said undesired chlorinated organic by-products. One of these methods involves the hydrochlorination of the hexadienes present in the crude allyl chloride feed, with HCl in the presence of a Lewis acid such as $MoCl_5$, to monochlorohexenes and dichlorohexanes. The boiling points, at atmospheric pressure, of the monochlorohexenes and dichlorohexanes being in the ranges of 110°–140° C. and 170°–220° C. respectively, they are much easier to separate from the allyl chloride (boiling point 45° C.) than are the hexadienes (boiling point 55°–65° C.).

Although WO-94/1316 shows the hydrochlorination treatment to be very effective in selectively converting to monochlorohexenes and dichlorohexanes as much as 98% of the hexadienes present in the allyl chloride feed, in practice this method has the drawbacks that the catalyst used is expensive and that it has to be separated from the reaction product. Also, conversion of the hexadienes in the allyl chloride to products which are even heavier than the monochlorohexenes and dichlorohexanes would be welcome. Of course, this conversion has to remain selective to the hexadiene, without unduly affecting the allyl chloride itself.

The crude allyl chloride also contains as by-products, in addition to the hexadienes, smaller amounts of other aliphatic and cycloaliphatic hexene and hexadiene isomers, such as normal hexenes, methylpentenes, methylcyclopentenes and methylcyclopentadienes and these are also carried on to the conventionally purified allyl chloride. The methylcyclopentene impurities, when present, were found to be converted in the epichlorohydrin production process to epoxymethylcyclopentanes which, if present in appreciable amounts, could affect the further processing of the epichlorohydrin.

It has now been found that the hexadienes, as well as the methylcyclopentenes and the other aliphatic and cycloaliphatic hexene and hexadiene isomers present in the crude allyl chloride and in the conventionally purified allyl chloride, can be effectively and efficiently removed by chlorination with molecular chlorine, in the liquid phase. In this chlorination step, the hexadienes are converted to dichlorohexenes and tetrachlorohexanes, which are heavier and thus even easier to separate from the allyl chloride mainstream than are the hydrochlorination products mentioned in WO-94/1316. The methylcyclopentenes in turn are converted in this chlorination step to dichloro methylcyclopentanes, which can also be easily separated from the allyl chloride mainstream. Surprisingly, it was found that the chlorination, when performed correctly, is very selective—in that the allyl chloride itself is not chlorinated to a substantial amount, although it is present in great excess to the unsaturated $C_6$ impurities.

SUMMARY OF THE INVENTION

The present invention is directed to a process for the removal of (cyclo)aliphatic hexene and hexadiene isomers from allyl chloride comprising a chlorination step which is performed in the liquid phase.

DETAILED DESCRIPTION

In the chlorination step molecular chlorine, which optionally can be mixed with an inert gas or with an inert liquid solvent such as 1,2,3 trichloropropane or carbon tetrachloride, is contacted in a reactor with the crude allyl chloride which is kept liquid in the combination of temperature and pressure employed. It is important that the allyl chloride be kept liquid, since only then the chlorination reaction is sufficiently selective. Gaseous allyl chloride reacts too readily with the chlorine to trichloropropane, which is not useful.

The temperature wherein the chlorination step according to the invention is performed can be varied within the ranges of from −20° to 100° C., and the pressure is chosen such as to ensure that the allyl chloride is liquid at the temperature employed.

The total amount of chlorine used for the chlorination according to the invention is preferably between 1 and 5, more preferably between 1.5 and 3.5, mol per mol of combined (cyclo)aliphatic hexenes and hexadienes originally present in the crude allyl chloride. A substantially higher concentration of chlorine than is needed for the optimal chlorination of the hexenes and hexadienes will tend, after chlorinating all of the impurities, to proceed and chlorinate the allyl chloride itself.

Crude allyl chloride often also contains residual propene from which the allyl chloride was made. Since the propene will also react with chlorine (to dichloropropane) under the reaction conditions, and since the direct removal of propene by conventional separation means such as distillation does not present the same difficulties as the removal of hexadienes and methyl cyclopentenes, it is convenient to separate the propene from the crude allyl chloride before effecting the chlorination step according to the invention. Therefore, in a preferred embodiment of the present invention, the chlorination step is performed after the light ends removal from the crude allyl chloride.

The purification step according to the invention can be performed batchwise as well as continuously.

After the chlorination step according to the invention is performed, the allyl chloride purification can be completed by conventional means, such as distillation. Therefore, in a preferred embodiment, the present invention comprises the steps of:

a. distillation of the crude allyl chloride to remove light ends;
b. chlorination in the liquid phase of the (cyclo)aliphatic hexene and hexadiene isomers present in the crude allyl chloride; and
c. distillation of the crude allyl chloride to remove heavy ends.

The following Examples will illustrate the invention.

The invention is further illustrated by the following nonlimiting examples.

EXAMPLE 1

16.7 g of feed A, laboratory grade allyl chloride containing 0.36 mol % of 1,5-hexadiene and a total of 0.46 mol % of (cyclo)aliphatic hexenes and hexadienes in >98 wt % of allyl chloride (Merck, Art. 800257) was placed in a 30 ml glass bottle at 21° C. and atmospheric pressure. The liquid was agitated using a magnetic stirrer. Chlorine gas was dosed via a pipe under the liquid surface, at a rate of 5 mg/sec. The product was analyzed by gas chromatography/mass spectrometry. The overall chlorination of hexadiene (to dichlorohexene and tetrachlorohexane) and allyl chloride (to 1,2,3-trichloropropane), after dosing 1 and 2 mole equivalents of chlorine on the total of (cyclo)aliphatic hexenes and hexadienes, are presented in Table 1.

EXAMPLES 2 AND 3

Feed A was fed continuously at 400 g/h and 20° C. to the bottom of a vertically positioned glass pipe reactor (4 mm diameter, 1 m length).

Chlorine gas was bubbled through the allyl chloride by feeding it continuously, at a rate of 0.92–4.70 g/h, amounting to molar ratios of between 0.6–2.7 on the total of (cyclo)aliphatic hexenes and hexadienes, to the bottom of the reactor, through a fine nozzle positioned just below a glass sinter positioned 3 cm from the bottom and reaching across the entire cross-section of the reactor. Reactor pressure below the sinter and at the reactor top was 160–180 kPa and atmospheric, respectively. Liquid samples were removed from the reactor top and analyzed by gas chromatography/mass spectrometry for their content of chlorinated products of hexadienes (dichlorohexenes and tetrachlorohexanes, combined) and allyl chloride (trichloropropane). The overall chlorination results are also presented in Table 1.

EXAMPLE 4

Similar to Examples 2 and 3, except that crude allyl chloride was used, containing 78 wt % of allyl chloride, 0.33 mol % of 1,5-hexadiene on allyl chloride and a total of 0.45 mol % of (cyclo)aliphatic hexenes and hexadienes, which feed was first distilled to remove propene (Feed B). The overall chlorination results are also presented in Table 1.

EXAMPLE 5

Similar to Example 4, except that the allyl chloride content of the crude product used, also after removing propene, was 80 wt %, the hexadiene content 0.31 mol % and the total (cyclo)aliphatic hexenes and hexadienes content 0.44 mol % (Feed C). The overall chlorination results are also presented in Table 1. Furthermore, the products balance of the hexadiene converted (to dichlorohexene and tetrachlorohexane) is detailed in Table 2.

From these Examples 1–5 it appears, that the chlorination reaction is selective up to the point that almost all of the hexadiene is chlorinated.

TABLE 1

| Overall chlorination in Examples 1–5 | | | | |
|---|---|---|---|---|
| Example | | Chlorine dosed, mol/mol hexenes | mol % chlorinated | |
| No. | Feed | and hexadienes | of hexadiene | of allyl chloride |
| 1 | A | 1.0 | 66.0 | 0.09 |
|   |   | 2.0 | 97.0 | 0.27 |
| 2 | A | 0.6 | 6.2 | 0.16 |
|   |   | 0.9 | 35.0 | 0.21 |
|   |   | 1.6 | 78.0 | 0.25 |
|   |   | 2.7 | 96.4 | 0.49 |
| 3 | A | 1.0 | 47.3 | 0.16 |
|   |   | 1.4 | 75.1 | 0.20 |
|   |   | 1.6 | 84.0 | 0.24 |
|   |   | 1.7 | 94.7 | 0.26 |
|   |   | 1.9 | 94.9 | 0.31 |
|   |   | 2.7 | 98.9 | 0.61 |
| 4 | B | 1.2 | 36.9 | 0.10 |
|   |   | 1.5 | 58.5 | 0.11 |
|   |   | 1.7 | 71.3 | 0.12 |
|   |   | 2.1 | 79.4 | 0.13 |
|   |   | 2.2 | 86.9 | 0.14 |
|   |   | 2.7 | 96.0 | 0.17 |
|   |   | 3.4 | 99.0 | 0.26 |
| 5 | C | 1.4 | 50.1 | 0.09 |
|   |   | 1.5 | 50.2 | 0.13 |

TABLE 1-continued

Overall chlorination in Examples 1-5

| Example No. | Feed | Chlorine dosed, mol/mol hexenes and hexadienes | mol % chlorinated | |
|---|---|---|---|---|
| | | | of hexadiene | of allyl chloride |
| | | 1.7 | 70.3 | 0.11 |
| | | 2.2 | 87.5 | 0.13 |
| | | 2.7 | 96.3 | 0.17 |
| | | 3.3 | 99.9 | 0.28 |

TABLE 2

Hexadiene product balance of Example 5

| Chlorine dosed mol/mol hexenes and hexadienes | % of original hexadiene in product, as | | | |
|---|---|---|---|---|
| | hexadiene (unchanged) | dichloro-hexane | tetrachloro-hexane | total |
| 1.4 | 49.9 | 46.4 | 2.9 | 99.2 |
| 1.5 | 49.8 | 44.1 | 3.3 | 97.2 |
| 1.7 | 29.7 | 62.0 | 6.6 | 98.3 |
| 2.2 | 12.5 | 70.4 | 13.6 | 96.5 |
| 2.7 | 3.7 | 69.4 | 24.1 | 97.2 |
| 3.3 | 0.1 | 47.7 | 46.0 | 93.8 |

We claim:

1. A process for the removal of (cyclo)aliphatic hexene and hexadiene isomers from allyl chloride comprising chlorinating a mixture of allyl chloride and impurities comprising (cyclo)aliphatic hexene and hexadiene isomers wherein said mixture is present in the liquid state, and removing chlorinated impurities from said allyl chloride wherein the chlorination step is performed with chlorine gas.

2. The process of claim 1, wherein the chlorination step is performed with a mixture of gaseous chlorine and an inert gas.

3. The process of claim 1 wherein chlorine is dissolved in an inert liquid.

4. The process of claim 1 wherein said chlorination step is performed at a temperature of between −20° and 100° C. and at a pressure which is sufficient to ensure that the allyl chloride is liquid at the temperature employed.

5. The process of claim 1 wherein the amount of chlorine used in the chlorination step is between 1 and 5 mol per mol of the impurities in said mixture.

6. The process of claim 5 wherein the amount of chlorine used is between 1.5 and 3.5 mol per mol of the impurities in said mixture.

* * * * *